US00PP23488P3

(12) United States Plant Patent

Deng et al.

(10) Patent No.: US PP23,488 P3

(45) Date of Patent: Mar. 19, 2013

(54) *GERBERA* PLANT NAMED 'UFGE 7015'

(50) Latin Name: *Gerbera hybrida*
Varietal Denomination: UFGE 7015

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 4 days.

(21) Appl. No.: 13/068,352

(22) Filed: May 9, 2011

(65) Prior Publication Data

US 2012/0291166 P1 Nov. 15, 2012

(51) Int. Cl.
*A01H 5/00* (2006.01)

(52) U.S. Cl. ..... Plt./357

(58) Field of Classification Search ..... Plt./357
See application file for complete search history.

*Primary Examiner* — Susan McCormick Ewoldt

(57) ABSTRACT

A new *Gerbera* plant particularly distinguished by having a novel combination of medium lengths of peduncles, double bright white inflorescence with a pink undertone, an overall inflorescence diameter of approximately 10.5 cm, a high level of resistance to powdery mildew, and demonstrated potential to produce attractive plants in large (≧20-cm in diameter) containers, is disclosed.

3 Drawing Sheets

Genus and species: *Gerbera hybrida*.
Variety denomination: 'UFGE 7015'.

BACKGROUND OF THE NEW PLANT

The invention relates to a new and distinct variety of *Gerbera hybrida* plant named 'UFGE 7015'. 'UFGE 7015' originated from a cross made at Wimauma, Fla. in 2005 between the female parent, 'Sunburst Snow White' (unpatented), and the male parent, 'UFGE 4033' (unpatented), an unreleased breeding line selected in Bradenton, Fla. in 2004 from a population of progeny of the cross 'UFGE 31-19' (unpatented) and 'UFGE 35-4' (unpatented). 'UFGE 7015' was selected by the inventors from the progeny of the stated parentage in summer 2007 at Wimauma, Fla. The first asexual reproduction of 'UFGE 7015' was accomplished when crown division was done in fall 2007 at Wimauma, Fla. Plants of 'UFGE 7015' have been asexually propagated by crown division and/or tissue culture for more than three generations. Asexually propagated plants of 'UFGE 7015' have remained true to the original selected plant, and all characteristics of the plant have been transmitted and retained through three successive asexual vegetative generations.

Plant Breeder's Rights for this cultivar have not been applied for. 'UFGE 7015' has not been made publicly available more than one year prior to the filing of this application.

SUMMARY OF THE INVENTION

The new and distinct variety of *Gerbera* plant is characterized by a novel combination of medium lengths of peduncles, double bright white inflorescences, an overall inflorescence diameter of approximately 10.5 cm, a high level of resistance to powdery mildew, and demonstrated potential to produce attractive plants in large (≧20-cm in diameter) containers. 'UFGE 7015' has not been observed under all possible environmental conditions. Its phenotype may vary significantly with variations in environment such as light intensity, temperature, and day length. The following are the most outstanding and distinguishing characteristics of this new cultivar when grown at Wimauma, Fla. under normal horticultural practices in greenhouse conditions which closely approximate those generally used in commercial practice.

1. Peduncle length of approximately 39 cm;
2. Double inflorescence type;
3. White (RHS 155D) ray florets with a pink undertone (RHS 36D);
4. Yellow-green (RHS 151D) discs before opening of disc florets;
5. White (RHS 155D) perianth lobe of disc florets;
6. Inflorescence diameter of approximately 10.5 cm; and
7. High resistance to powdery mildew.

DESCRIPTION OF THE PHOTOGRAPHS

This new *Gerbera* plant is illustrated by the accompanying photographs which show the plant's form, inflorescences, and foliage. The colors shown are as true as can be reasonably obtained by conventional photographic procedures. The photographs are of a plant approximately 4 months old which was produced from one tissue culture liner and is potted in a 2.7-L container. Colors in the photograph may differ slightly from the color values cited in the detailed botanical description, which accurately describe the colors of the new *Gerbera*.

DESCRIPTION OF THE NEW CULTIVAR

Figure 1:
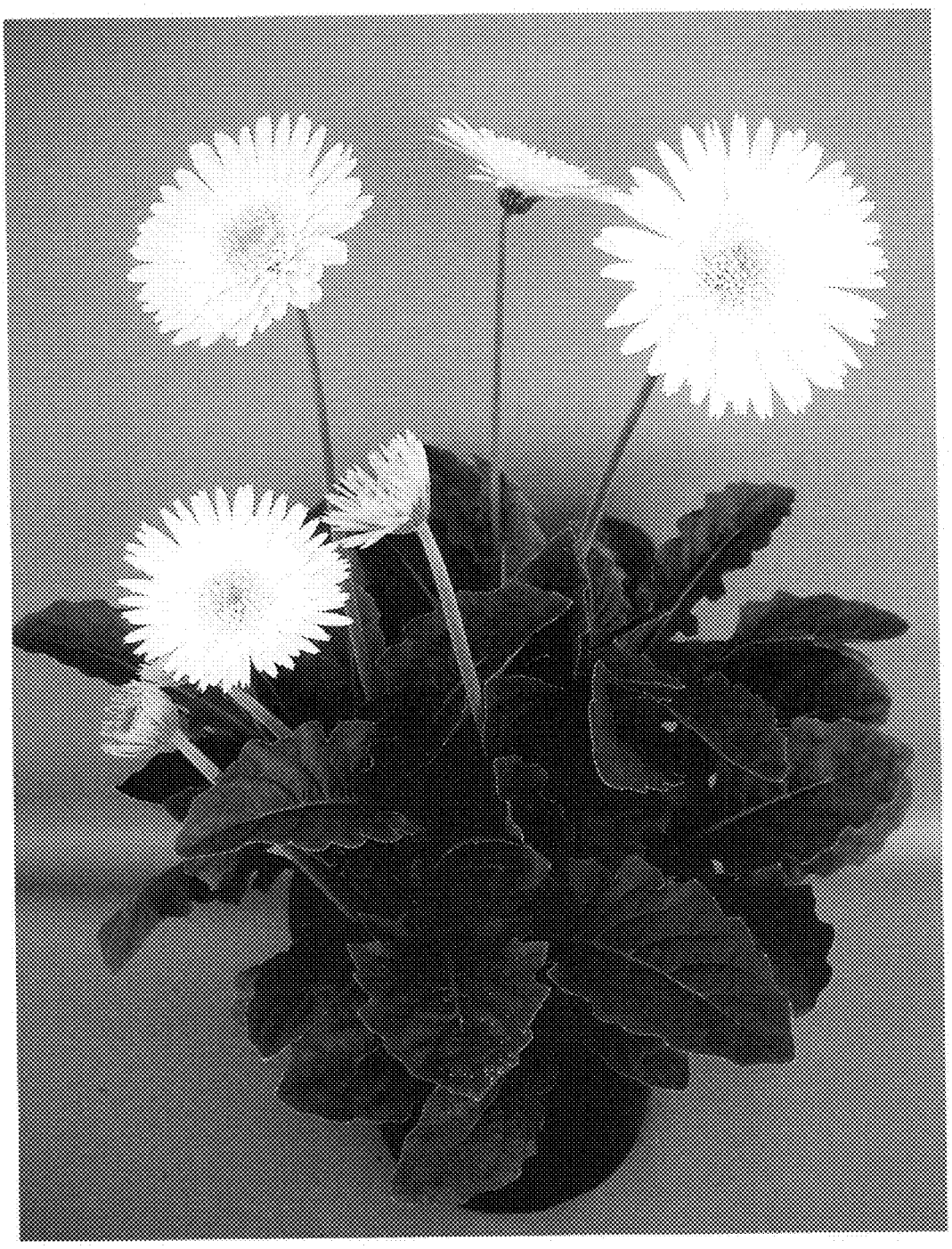
FIG. 1 shows the overall plant habit including inflorescences and foliage and is taken from a side perspective view.
Figure 2:
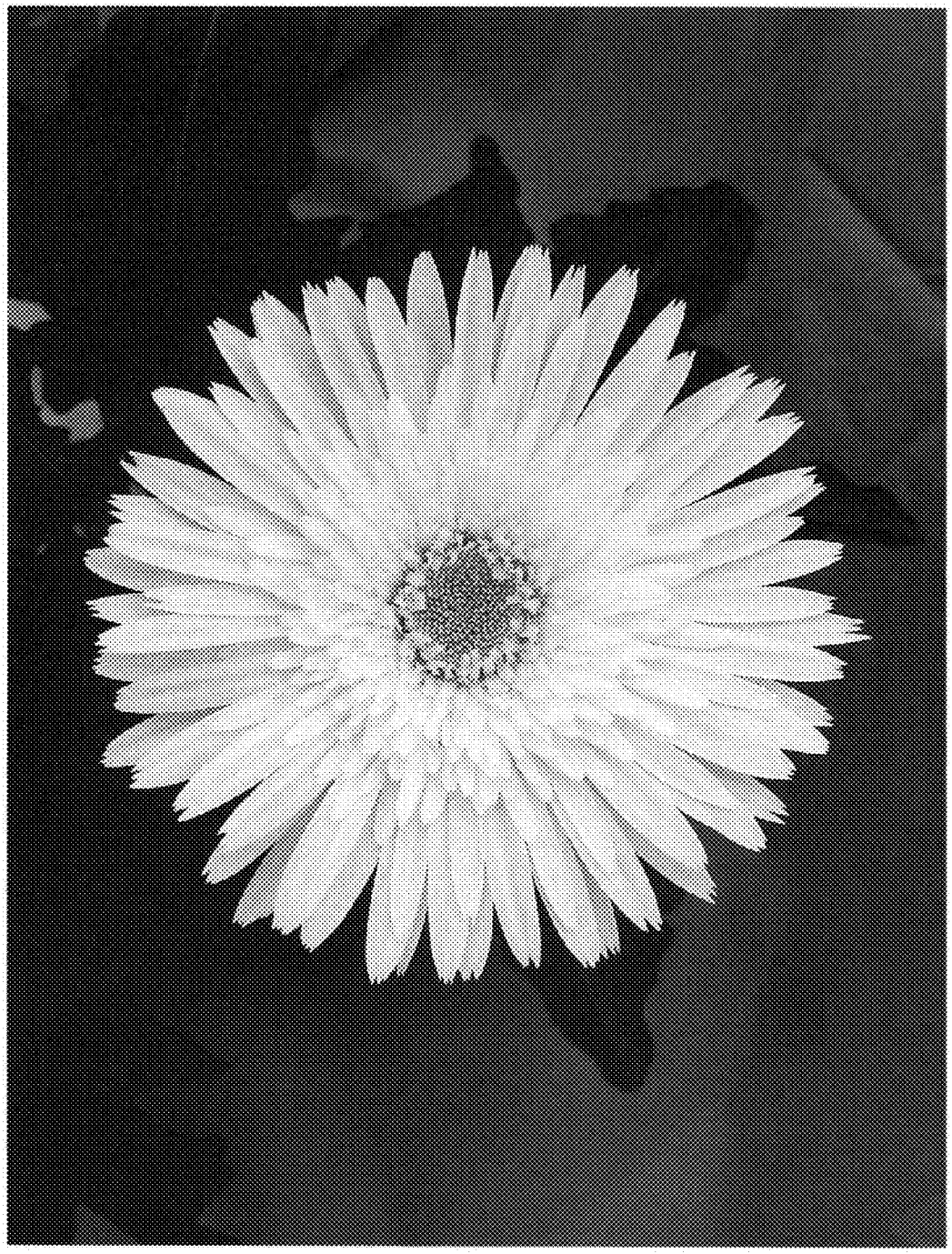
FIG. 2 shows a close-up of the inflorescence.
Figure 3:
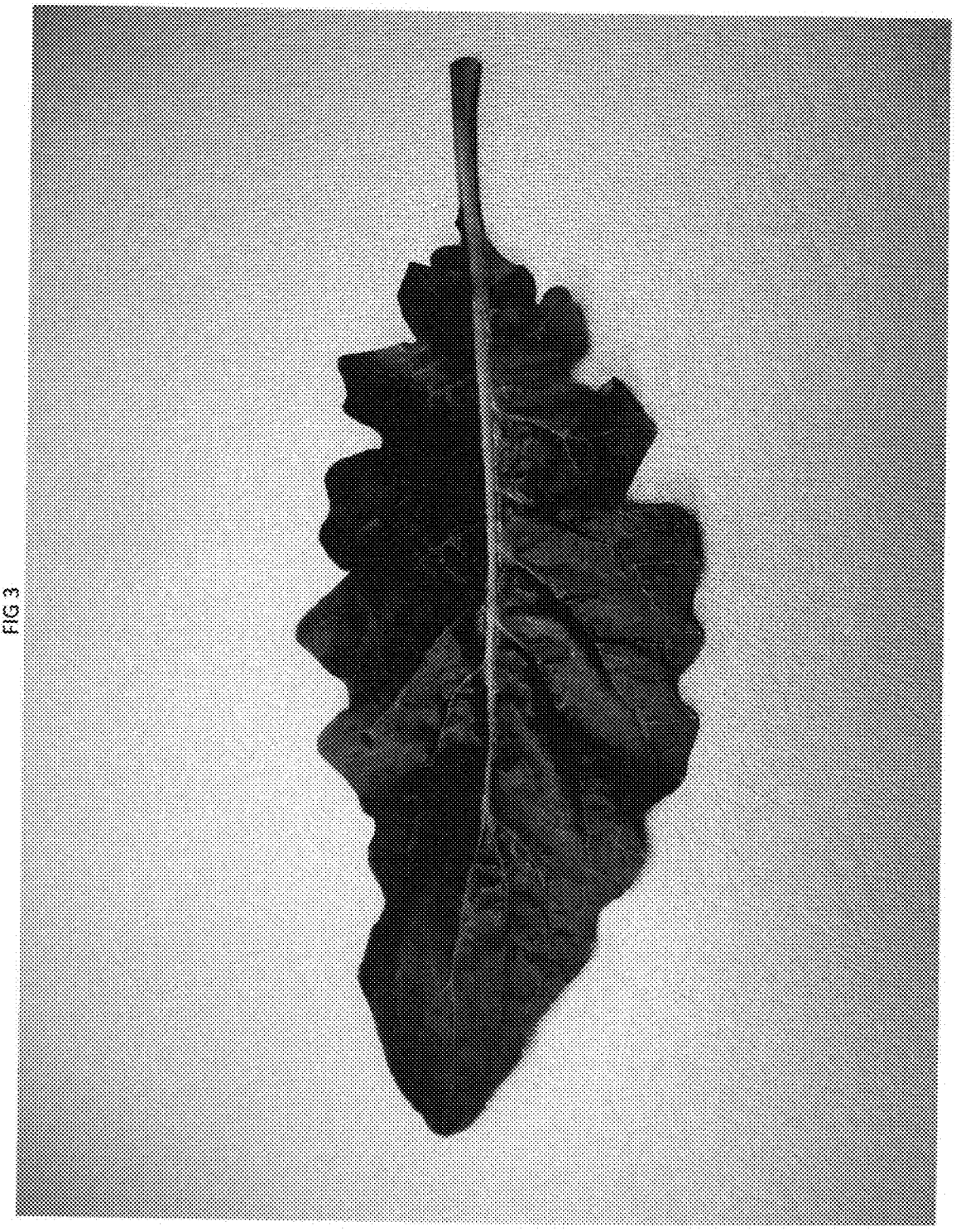
FIG. 3 shows a close-up of the typical leaf.

The following detailed description sets forth the distinctive characteristics of 'UFGE 7015'. The present botanical description is that of the variety at approximately 4 months old on Nov. 23, 2009 at 11:30 a.m. in a room under north light at Wimauma, Fla. The colors (except those in common terms) are described from R.H.S. Colour Chart published by The Royal Horticultural Society in London (1986 ed.), in association with the Flower Council of Holland.

DETAILED BOTANICAL DESCRIPTION

Classification:

*Botanical.*—*Gerbera hybrida* cv. 'UFGE 7015'.

*Common name.*—*Gerbera.*

Parentage:

*Female, or seed, parent.*—'Sunburst Snow White' (unpatented).

*Male, or pollen, parent.*—'UFGE 4033' (unpatented).

Inflorescence:

*Appearance.*—Full-double type inflorescence form; solitary inflorescences borne on upright and strong peduncles (or scapes) above the foliar plane; ray and disc florets arranged acropetally on a capitulum.

*Type.*—Double.

*Diameter.*—Medium, approx. 105 mm.

*Color* (*general tonality from a distance of* 3 *meters*).—White (RHS 155D) with a pink undertone (RHS 36D).

*Shape.*—Incurving funnel-shaped.

*Fragrance.*—None detected.

*Flowering season.*—Plants begin flowering about seven and half weeks after planting and flower year-round in outdoor gardens in Wimauma, Fla., until plants are killed by frosts or freezes; plants flower year-round under greenhouse conditions in Wimauma, Fla.

*Inflorescence longevity.*—Inflorescences last about two to three weeks on the plant in Wimauma, Fla.; inflorescences not persistent.

*Quantity of inflorescences.*—Free flowering habit, with up to 14 open and developing inflorescences per plant at one time.

*Inflorescence bud.*—Height: About 1.3 cm. Diameter: About 2.1 cm. Shape: Oblate. Color (opening buds): Close to yellow-green (RHS 151D).

*Inflorescence size.*—Depth (height): About 1.8 cm. Diameter of disc: About 2.3 cm. Receptacle height: About 2 mm. Receptacle diameter: About 1.3 cm. Receptacle color: Close to green-white (RHS 157A).

*Phyllaries.*—Number of phyllaries per inflorescence: About 75 arranged in about three whorls. Length: About 1.2 cm. Width: About 2 mm. Shape: Subulate. Apex: Narrowly acute. Base: Truncate. Margin: Entire. Texture, upper surface: Smooth, glabrous. Texture, lower surface: Moderately tomentose. Color, upper surface: Close to green (RHS 144A). Color, lower surface: Close to green (RHS 137C). Color, towards the base: Close to green (RHS 137B).

*Inner ray florets.*—Number per inflorescence: About 155 arranged in about six whorls. Length: About 2.7 cm. Width: About 3 mm. Shape: Narrow elliptic. Apex: Emarginate to obtuse. Base: Truncate. Margin: Entire. Texture, upper surface: Smooth, glabrous, slightly velvety, longitudinally ridged. Texture, lower surface: Smooth, glabrous, slightly velvety, longitudinally ridged. Color, fully opened upper surface: Close to white (RHS 155D) and undertones of red (RHS 36D). Color, fully opened lower surface: Close to white (RHS 155D). Longitudinal axis of outer row: Straight. Longitudinal axis of inner rows: Straight. Longitudinal axis of ray female floret: Moderately incurving.

*Outer ray floret.*—Cross section: Concave. Number: About 62 arranged in three whorls. Length: Medium, approx. 39 mm. Width: Medium, approx. 6-7 mm. Shape: Narrow elliptic. Apex: Emarginate to obtuse. Base: Truncate. Margin: Entire. Depth of incision: Medium-deep. Texture, upper surface: Smooth, glabrous, slightly velvety, longitudinally ridged. Texture, lower surface: Smooth, glabrous, slightly velvety, longitudinally ridged. Color (topside): Close to white (RHS 155D) with undertone of red (RHS 36D). Color (bottom side): White (RHS 155D).

*Disc florets.*—Number: About 302. Length: About 1.5 cm. Width: About 3 mm. Shape: Tubular, fused. Apex: Narrowly obtuse. Base: Fused. Margin: Entire. Texture, upper and lower surfaces: Smooth, glabrous. Color, fully opened upper surface: Close to white (RHS 155D). Color, fully opened lower surface: Close to white (RHS 155D). Color, fully opened midsection: Close to white (RHS 155A). Color, fully opened base: Close to white (RHS 155B). Disc diameter: Medium, approx. 26 mm.

*Reproductive organs.*—Androecium: On disc floret only; quantity: one. Gynoecium: On ray and disc florets: quantity per floret: one. Filament length: About 4 mm. Filament color: Close to white (155B). Anther shape: Linear. Anther length: About 4 mm. Anther width: About 1 mm. Pollen, amount: Prolific. Pollen color: Close to yellow (RHS 8B). Pistil: One per floret. Pistil length: About 1.6 cm. Stigma shape: Cleft. Style length: About 1 cm. Ovary, color: Close to green-white (RHS 157A). Style color, distally and proximally: Close to white (155B). Stigma color: Close to white (RHS 155D). Anther color: Close to yellow (RHS 9B). Color of top relative to other parts: Lighter. Longitudinal stripes: Absent.

*Pappus.*—Quantity of hairs per floret: About 73. Length: About 6 mm. Diameter: Less than 1 mm. Texture: Soft. Color: Close to yellow-white (RHS 158D). Color of top relative to other parts: Same. Level of top relative to closed disc florets: Above, 1-2 mm in center.

*Peduncle.*—Length: Medium, approx. 39 cm. Tendency to fasciation: Absent. Thickness: Medium, approx. 5 mm. Strength: Sturdy. Texture: Moderately densely tomentose. Color: Yellow-green (RHS 144B). Anthocyanin coloration: At base: Very weak. At top: Absent.

Plant:

*General appearance.*—Herbaceous perennial, typically grown as container or garden plants; upright and mounding growth habit, roughly globular in shape; leaves arranged in basal rosettes and outwardly arching; dense and bushy habit; inflorescences held above the foliar plane on sturdy and strong basal peduncles (or scapes); moderately vigorous.

*Plant height, soil level to top of foliar plane.*—Approx. 31 cm.

*Plant height, soil level to top of inflorescence.*—About 41 cm.

*Plant width.*—Approx. 45 cm.

*Foliage.*—Leaf arrangement: Basal rosette, alternate, simple. Leaf blade: Length: Approx. 23 cm. Width: Medium, approx. 11 cm. Shape: Oblong. Base: Truncate. Margin: Irregular crenate, sinuses divergent, undulate. Texture, upper surface: Sparsely pubescent. Texture, lower surface: Moderately pubescent. Venation pattern: Pinnate. Thickness: Medium. Blistering: Weak. Pubescence (On upper side, midrib excluded): Medium. Depth of incisions in leaf: Basal part: Deep.

Central part: Medium. Distal part: Shallow. Color: Upper side: Close to Green (RHS 137B). Bottom side: Close to Yellow-green (RHS 146B). Glossiness on upper side: Strong. Shape of apex: Moderately acute to obtuse.

*Petiole*.—Petiole length: Medium, approx. 7 cm. Diameter: About 4 mm. Texture, upper and lower surfaces: Moderately pubescent. Color of petiole: Yellow-green (RHS 144B). Anthocyanin coloration, at base: Strong, red-purple (RHS 70D).

Resistance to diseases: 'UFGE 7015' has been observed in multiple experiments in which it was compared with two common commercial cultivars, 'Pensacola' *gerbera* (unpatented) and 'Bimini' *gerbera* (unpatented), for the incidence and severity of powdery mildew, *Podosphaera* (syn. *Sphaerotheca*) *fusca* (Fr.) S. Blumer. 'UFGE 7015' has consistently been found to have a high level of resistance to powdery mildew. In one experiment (Experiment 1), conducted in winter 2008 and spring 2009 at Wimauma, Fla., tissue culture liners of 'UFGE 7015', 'Bimini', and 'Pensacola' were transplanted on into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Plants were grown under a plastic tunnel within a screen house with approximately 45% light exclusion. Fungicides were not applied throughout the experiments to subject the plants to natural powdery mildew disease pressures. In Experiment 1, the severity of powdery mildew on *gerbera* leaves was assessed at week 8 after transplanting (Feb. 4, 2009), week 10 after transplanting (Feb. 18, 2009), week 12 after transplanting (Mar. 4, 2009), and week 14 after transplanting (Mar. 18, 2009). A randomized complete block design was used with five replications. The experimental unit was a single containerized plant. 'UFGE 7015' showed a high level of resistance to powdery mildew in Experiment 1 (Table 1). 'UFGE 7015' remained to be more productive than 'Bimini' and 'Pensacola' when natural powdery mildew disease pressure existed (Table 1). No other disease resistance characterizations have been made.

TABLE 1

Powdery mildew (PM) severity ratings and inflorescence counts of 'UFGE 7015' and two commercial gerbera cultivars, 'Bimini' and 'Pensacola', grown under natural powdery mildew pressure in Experiment 1 (Winter 2008 through Spring 2009) in Wimauma, FL.

| | PM Ratings[Z] | | | | Inflorescence |
|---|---|---|---|---|---|
| Cultivars | Week 8 | Week 10 | Week 12 | Week 14 | counts[Y] |
| Experiment 1 (Winter 2008 through Spring 2009) | | | | | |
| 'UFGE 7015' | 1.0 | 1.8 | 2.4 | 3.6 | 7.6 |
| 'Bimini' | 1.2 | 1.8 | 5.4 | 8.0 | 3.2 |
| 'Pensacola' | 1.0 | 2.0 | 4.8 | 8.6 | 3.0 |

[Z]Powdery mildew severity was rated on a scale of 1 to 10 as described by Hausbeck et al. (2002): 1 = no disease, 2 = trace to 10%, 3 = 10% to 20%, 4 = 20 to 30%, 5 = 30% to 40%, 6 = 40% to 50%, 7 = 50% to 60%, 8 = 60% to 70%, 9 = 70% to 80%, and 10 = 80% to 100% of leaf surface covered with powdery mildew.

[Y]Total number of inflorescences produced per plant over nine weeks from Jan. 20, 2009 to Mar. 17, 2009 in Experiment 1 in a screen house in Wimauma, FL

COMPARISON WITH PARENTAL AND KNOWN CULTIVARS

'UFGE 7015' differs from the female parent 'Sunburst Snow White' (unpatented) by having tall (approximately 40 cm) plants, as opposed to short (approximately 20 cm) plants under growing conditions in Wimauma, Fla. 'UFGE 7015' differs from the male parent 'UFGE 4033' (unpatented) by having full double inflorescences, as opposed to semi-double inflorescences under growing conditions in Wimauma, Fla.

'UFGE 7015' can be compared to *Gerbera hybrida* 'UFGE 7014', disclosed in the co-pending application (Ser. No. 12/931,609). Although 'UFGE 7015' has the same parents with 'UFGE 7014', 'UFGE 7015' differs from 'UFGE 7014' in the following characteristics:

1. Ray florets of 'UFGE 7015' have a pink undertone while ray florets of 'UFGE 7014' are white;
2. Plants of 'UFGE 7015' are much more resistant to powdery mildew than plants of 'UFGE 7014'.
3. Inflorescences of 'UFGE 7015' are of the full-double type while inflorescences of 'UFGE 7014' are of the semi-double type.

Comparisons were made with the commercial *gerbera* variety 'Bimini' (unpatented) and the commercial *gerbera* variety 'Pensacola' (unpatented). One experiment was conducted in a greenhouse at Wimauma, Fla. under standard greenhouse management practices to evaluate the plant performance (days to flower, inflorescence quality, inflorescence count, and plant quality) of 'UFGE 7015' for container plant production in comparison to 'Bimini' and 'Pensacola'. In this plant performance experiment (Experiment 2), tissue culture liners were transplanted on Dec. 9, 2008 into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Potted plants were grown on metal benches in a glass house and spaced 46 cm×46 cm apart. Temperatures inside the greenhouse ranged from 18° C. to 33° C. Two hours of additional photoperiodic lighting were provided between Dec. 9, 2008 and Mar. 17, 2009. Fungicides and insecticides were applied as needed to control powdery mildew and western flower thrips. Inflorescence quality was rated on a 1 to 5 scale: 1=very poor, 3=fair, some blemishes, but acceptable, and 5=excellent, bright, uniform, and no blemishes. Inflorescence counts were recorded weekly from Jan. 20, 2009 through Mar. 17, 2009. Plant quality was rated three times, on Jan. 20, 2009, Feb. 3, 2009, and Feb. 17, 2009, using a 1 to 5 scale: 1=few leaves or long petioles, container surface visible, very poor and unacceptable as flowering pot plants, 3=fair and marketable, and 5=excellent, full, symmetrical, attractive plants.

The experiment design for Experiment 2 was a randomized complete block design with five replications. The experimental unit was a single containerized plant.

'UFGE 7015' came into flowering 11.8 to 16.6 days earlier than 'Bimini' and 'Pensacola' in Experiment 2 (Table 2). The inflorescence quality rating of 'UFGE 7015' was 4.5, similar to that of 'Bimini' (5.0), and higher than that of 'Pensacola' (4.1) (Table 2). 'UFGE 7015' produced more inflorescences (320% more than 'Bimini' and 686% more than 'Pensacola') (Table 2). The plant quality rating of 'UFGE 7015' was 4.8, higher than that of the controls (Table 2).

TABLE 2

Plant performance of 'UFGE 7015' and two commercial cultivars, 'Bimini' and 'Pensacola', grown in Experiment 2 (Winter 2008 through Spring 2009) in Wimauma, Florida.

| Cultivars | Days to 1st open inflorescence (no.) | Inflorescence quality[Z] | Inflorescence counts[Z] (no.) | Plant quality[Y] |
|---|---|---|---|---|
| Experiment 2 (Dec. 9, 2008 to Mar. 17, 2009) | | | | |
| 'UFGE 7015' | 52.2 | 4.5 | 9.6 | 4.8 |
| 'Bimini' | 64.0 | 5.0 | 3.0 | 3.1 |
| 'Pensacola' | 68.8 | 4.1 | 1.4 | 3.3 |

[Z]Inflorescence count data were collected over nine weeks from Jan. 20, 2009 to Mar. 17, 2009. Each value represents the mean of five replicates.
[Y]The plant quality rating value was the mean of five replicates over three times (Jan. 20, Feb. 3, and Feb. 17, 2009).

Literature Cited

Hausbeck, M. K., W. R. Quackenbush, and S. D. Linderman. 2002. Evaluation of cultivars of African daisy for resistance to powdery mildew, 2002. B&C Tests 18:O0004.

We claim:

1. A new and distinct cultivar of *Gerbera* plant named 'UFGE 7015', as illustrated and described herein.

* * * * *